United States Patent [19]

Monti et al.

[11] Patent Number: 5,227,137
[45] Date of Patent: Jul. 13, 1993

[54] VACUUM CLAMPED MULTI-SAMPLE FILTRATION APPARATUS

[75] Inventors: Patricia C. Monti, Silver Spring; Richard J. White, Laurel; Michael K. Nicholson, Cabin John, all of Md.

[73] Assignee: Nicholson Precision Instruments Inc., Gaithersburg, Md.

[21] Appl. No.: 924,795

[22] Filed: Aug. 6, 1992

Related U.S. Application Data

[63] Continuation of Ser. No. 680,544, Apr. 4, 1991, abandoned.

[51] Int. Cl.$^5$ .............................................. G01N 1/14
[52] U.S. Cl. ...................................... 422/101; 422/58; 422/102; 422/103; 436/178; 436/180; 436/809; 435/301; 435/310; 435/311; 210/406; 210/416.1; 210/474; 210/477
[58] Field of Search ............... 422/101, 102, 103, 58; 436/165, 178, 180, 809; 435/300, 301, 310, 311, 809; 210/406, 416.1, 455, 474, 477

[56] References Cited

U.S. PATENT DOCUMENTS

| | | | |
|---|---|---|---|
| 3,956,125 | 5/1976 | Strutt et al. | 210/94 |
| 4,090,850 | 5/1978 | Chen et al. | 424/1 |
| 4,167,875 | 9/1979 | Meakin | 73/421 R |
| 4,219,530 | 8/1980 | Kopp et al. | 422/69 |
| 4,427,415 | 1/1984 | Cleveland | 422/101 |
| 4,493,815 | 1/1985 | Fernwood et al. | 422/101 |
| 4,704,255 | 11/1987 | Jolley | 422/101 |
| 4,726,932 | 2/1988 | Feier et al. | 422/103 |
| 4,777,021 | 10/1988 | Wertz et al. | 422/101 |
| 4,787,988 | 11/1988 | Bertoncini et al. | 210/808 |
| 4,797,259 | 1/1989 | Matkovich et al. | 435/301 |
| 4,822,741 | 4/1989 | Banes | 435/300 |
| 4,828,801 | 5/1989 | Lombardy et al. | 422/102 |
| 4,834,946 | 5/1989 | Levin | 422/101 |
| 4,839,292 | 6/1989 | Cremonese | 435/313 |
| 4,846,970 | 7/1989 | Bertelsen et al. | 210/232 |
| 4,859,419 | 8/1989 | Marks et al. | 422/56 |
| 4,874,691 | 10/1989 | Chandler | 435/7 |
| 4,895,706 | 1/1990 | Root et al. | 422/102 |
| 4,902,481 | 2/1990 | Clark et al. | 422/101 |
| 4,908,319 | 3/1990 | Smyczek et al. | 435/285 |
| 4,927,604 | 5/1990 | Mathus et al. | 436/178 |
| 4,948,564 | 8/1990 | Root et al. | 422/101 |
| 4,978,507 | 12/1990 | Levin | 422/100 |

*Primary Examiner*—Lynn M. Kryza
*Attorney, Agent, or Firm*—Sterne, Kessler, Goldstein & Fox

[57] ABSTRACT

An apparatus for filtering multiple biological samples using a filter membrane is disclosed. The apparatus comprises a base plate, a well plate, a gasket, and a first vacuum member for vacuum-clamping the base plate, well plate, gasket and filter membrane together. The apparatus may further comprise a second vacuum member for drawing the biological samples from the well plate into contact with the filter membrane.

17 Claims, 5 Drawing Sheets

VACUUM CLAMPED MULTI-SAMPLE FILTRATION APPARATUS

This application is a continuation of application Ser. No. 07/680,544, filed Apr. 4, 1991, now abandoned.

BACKGROUND OF THE INVENTION

1. Field of the Invention

This invention relates generally to an apparatus and method thereof for biochemical testing and screening. More particularly, the present invention relates to a multi-sample filtration apparatus and method thereof for biomedical testing and screening of multiple samples.

2. Related Art

Multi-sample filtration apparatus are generally used for sampling all types of media. For example, in molecular biology applications, the testing of extracts of blood, extracts of cells or purified nucleic acids from a variety of sources is a common application of the apparatus. In the area of immunology, the testing of extracts of blood, whole cells or purified materials are common applications.

Conventional apparatus typically operate by allowing a sample to come into contact with a filter membrane. Tests are then performed on the membrane, and a variety of determinations can be made regarding the sample media. Conventional filtration devices further allow for testing of multiple samples, so as to allow more than one type of media or multiple samples of identical media to be tested.

One type of multi-sample filtration apparatus, disclosed in U.S. Pat. No. 4,493,815 to Fernwood et al (referred to herein as the "Fernwood Patent") employs a vacuum member to draw the media into contact with a filter membrane. The purpose of the vacuum member is to bring the media in contact with the filter membrane. The Fernwood Patent also discloses a plurality of mechanical screws for "sandwiching" (clamping) the assembly together. Clamping of the assembly is necessary to prevent migration of samples on the membrane and leakage of vacuum.

Apparatus such as that disclosed by the Fernwood Patent, however, have several disadvantages. One disadvantage relates to sealing. If a good seal is not obtained, samples will migrate across the filter membrane causing serious problems when a lab technician is trying to analyze the membrane. Some samples will be destroyed, others will be placed in a condition that will not readily facilitate analysis by the technician.

Another disadvantage relates to operation of the apparatus. Conventional methods of manually creating a seal are cumbersome. Screws and clamps must be fastened and unfastened, parts must be taken apart. Use of screw and clamp is inefficient and creates a significant loss in production output.

SUMMARY OF THE INVENTION

The present invention is directed to overcoming one or more of the problems set forth above. In one embodiment, the present invention is an apparatus for testing sample media using a filter membrane. The apparatus first comprises a well plate configured in a standard 96 well microtiter configuration. Each well is adapted to contain the sample media.

The apparatus further comprises a first means for vacuum-clamping the filter membrane in sealable contact with the well plate. The vacuum clamping means seals each of the wells of the well plate in contact with the filter membrane.

The apparatus further comprises a second means for drawing the sample media contained in each well of the well plate into contact with the filter membrane.

The vacuum clamping means comprises a vacuum clamping valve and a first vacuum inlet mounted on a base plate. The vacuum inlet is adapted to connect with an external vacuum source. The vacuum clamping valve is rotatable to a first position where the vacuum clamping valve is in an "on" position and a second position where the vacuum clamping valve is in an "off" position. When the vacuum clamping valve is in said "on" position, the first vacuum inlet is in communication with a second channel to supply a vacuum to a vacuum clamping region of the apparatus.

The vacuum clamping means may further comprise a gasket. The gasket has first and second substantially parallel elastomeric surfaces and a plurality of wells in registration with wells of the well plate.

The base plate has formed therein a vacuum reservoir surrounded by a plurality of islands. The gasket is mounted about the islands of the base plate to form the vacuum clamping area.

The vacuum clamping feature of the present invention provides several advantages heretofore unavailable in conventional media testing apparatus. One such advantage relates to the resultant sample media on the filter membrane. In particular, the vacuum clamping feature provides a more consistent clamping force than that of the screws and clamps used in conventional apparatus. A consistent clamping force ensures that each of the sample media will be properly placed on the filter membrane. A second advantage relates to operation. More particularly, the vacuum clamping feature makes operation of the present invention significantly easier than conventional apparatus. Ease of operation leads to increased production output and efficiency.

BRIEF DESCRIPTION OF THE DRAWINGS

The following detailed description of the present invention will be more fully understood with reference to the accompanying drawings, in which.

DETAILED DESCRIPTION OF THE PREFERRED EMBODIMENTS

In one embodiment, the present invention is an apparatus configured to sample media. One feature of the present invention is a first vacuum member adapted to bring the media in contact with a filter membrane. A second feature of the present invention is a second vacuum member adapted to provide the clamping force necessary to seal the apparatus so that the first vacuum member can properly bring the media in contact with the filter membrane.

As will become obvious to one skilled in the art, the vacuum clamping feature of the present invention provides several advantages heretofore unavailable in conventional media testing apparatus. One such advantage relates to the resultant sample media on the filter membrane, In particular, the vacuum clamping feature provides a more consistent clamping force than that of the screws and clamps used in conventional apparatus. A consistent clamping force ensures that each of the sample media will be properly placed on the filter membrane. A second advantage relates to operation. More particularly, the vacuum clamping feature makes operation of the present invention significantly easier than conventional apparatus. Ease of operation leads to increased production output and efficiency.

Figure 1:
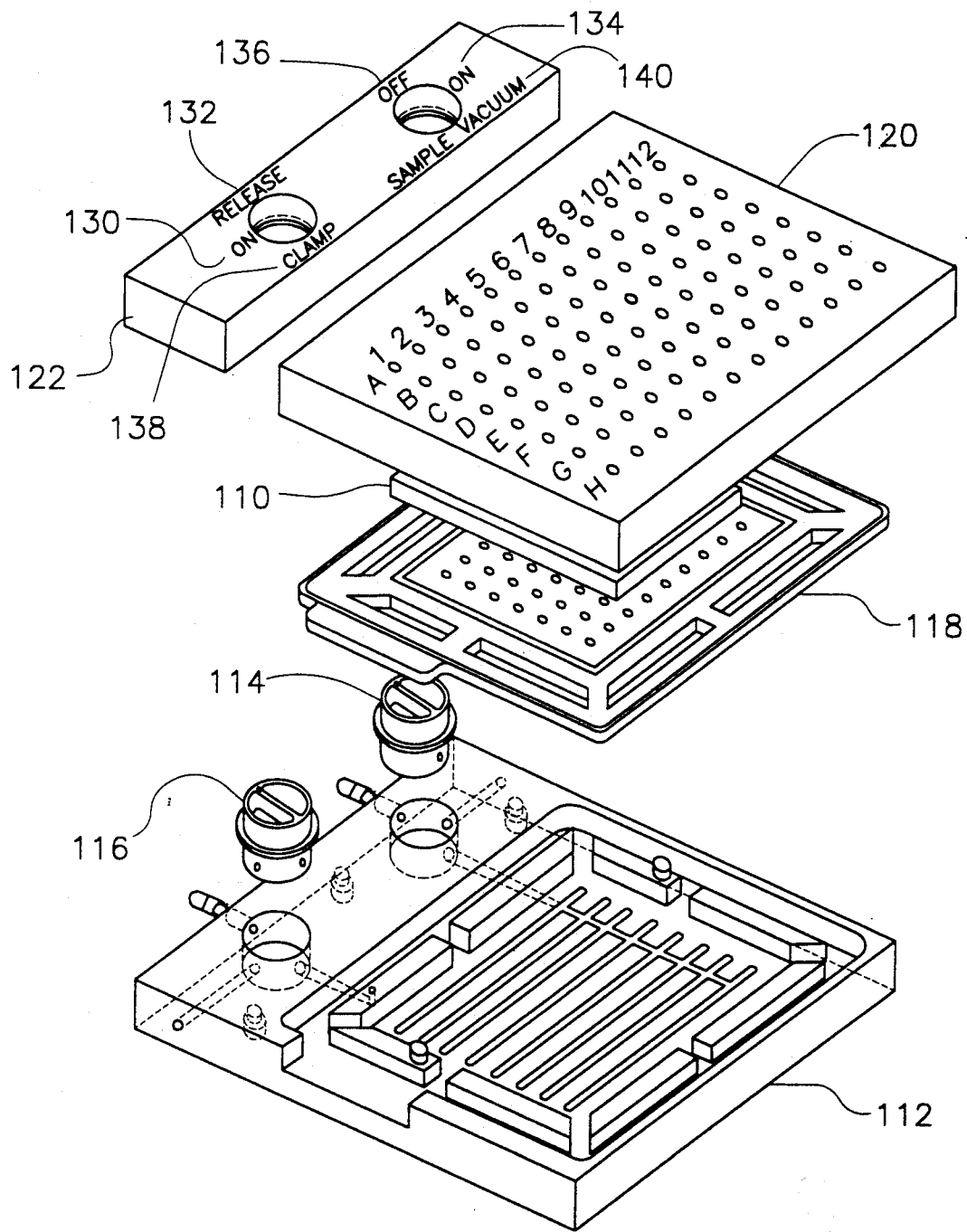
FIG. 1 is a exploded view of the present invention.

Referring first to FIG. 1, wherein an exploded view of the apparatus of the present invention is shown. The apparatus is identified by a reference numeral 100. The apparatus 100 generally comprises a filter membrane 110, a base plate 112, a first vacuum valve 114, a second vacuum valve 116, a gasket 118, a well plate 120, and a cover plate 122.

The filter membrane 110 is provided to receive and capture sample media. The filter membrane 110 is well known in the art. In the preferred embodiment, filter membrane 110 is made of either nylon or nitrocellulose. However, any type of filter membrane could potentially be used with the present invention. Such alternative filter membranes, include, but are not limited to, polyvinylidene fluoride membranes, cellulose acetate membranes, and modified nylon membranes.

The base plate 112 is generally configured to provide the two independent vacuum features. The first vacuum feature operates to bring the sample media contained in well plate 120 into contact with the filter membrane 110. The second vacuum feature operates to clamp the filter membrane 110, base plate 112, gasket 118, and well plate 120 assembly together. The second vacuum feature replaces the screw clamps found in conventional apparatus.

The first vacuum valve 114 is generally provided to regulate the first vacuum feature. As will be more fully described herein, the first vacuum valve 114 is configured to allow the user to control the rate at which the media samples are drawn into contact with the filter membrane 110. As shown by cover plate 122, the first vacuum valve 114 is rotatable to a first position where the vacuum valve 114 is in an "on" position 134 and a second position where the first vacuum valve 114 is in an "off" position 136. When the first vacuum valve 114 is in the "on" position 134, a vacuum is generated in the base plate 112 causing the sample media in the well plate 120 to be drawn into contact with the filter membrane 110.

The second vacuum valve 116 is generally provided to regulate the second vacuum feature. As will be more fully described herein, the second vacuum valve 116, allows the user to control the clamp force that holds the filter membrane 110, base plate 112, gasket 118, and well plate 120 assembly together. Application of the clamp force allows the apparatus 100 to be quickly assembled. Removal of the clamp force allows the apparatus 100 to be quickly disassembled. As also shown by the cover plate 122, the second vacuum valve 116 is rotatable to a first position where the second vacuum valve 116 is in an "on" position 130 and a second position where the second vacuum valve 116 is in a "release" position 132. When the second vacuum valve 116 is in the "on" position 130, a vacuum is generated in the base plate 112 causing the base plate 112/gasket 118/filter membrane 110/well plate 120 assembly to be securely held together.

The gasket 118 is generally provided to seal the apparatus 100 such that the first vacuum feature and the second vacuum feature can operate at optimum performance levels. As will be shown more fully herein, gasket 118 ensures that the necessary clamping force is maintained such that no leakage of vacuum occurs from the second vacuum feature during operation of the first vacuum feature. Prevention of vacuum leakage from the second vacuum feature during operation of the first vacuum feature is essential to ensuring that the sample media is properly disposed on the filter membrane 110. Failure to prevent vacuum leakage from the second vacuum feature may result in migration of sample media across the filter membrane 110.

The well plate 120 is generally provided to hold the sample media to be tested by the apparatus 100. As will be described more fully herein, well plate 120 may be configured in a conventional 96 well microtiter configuration thereby allowing multiple sample media to be tested.

Figure 2A:
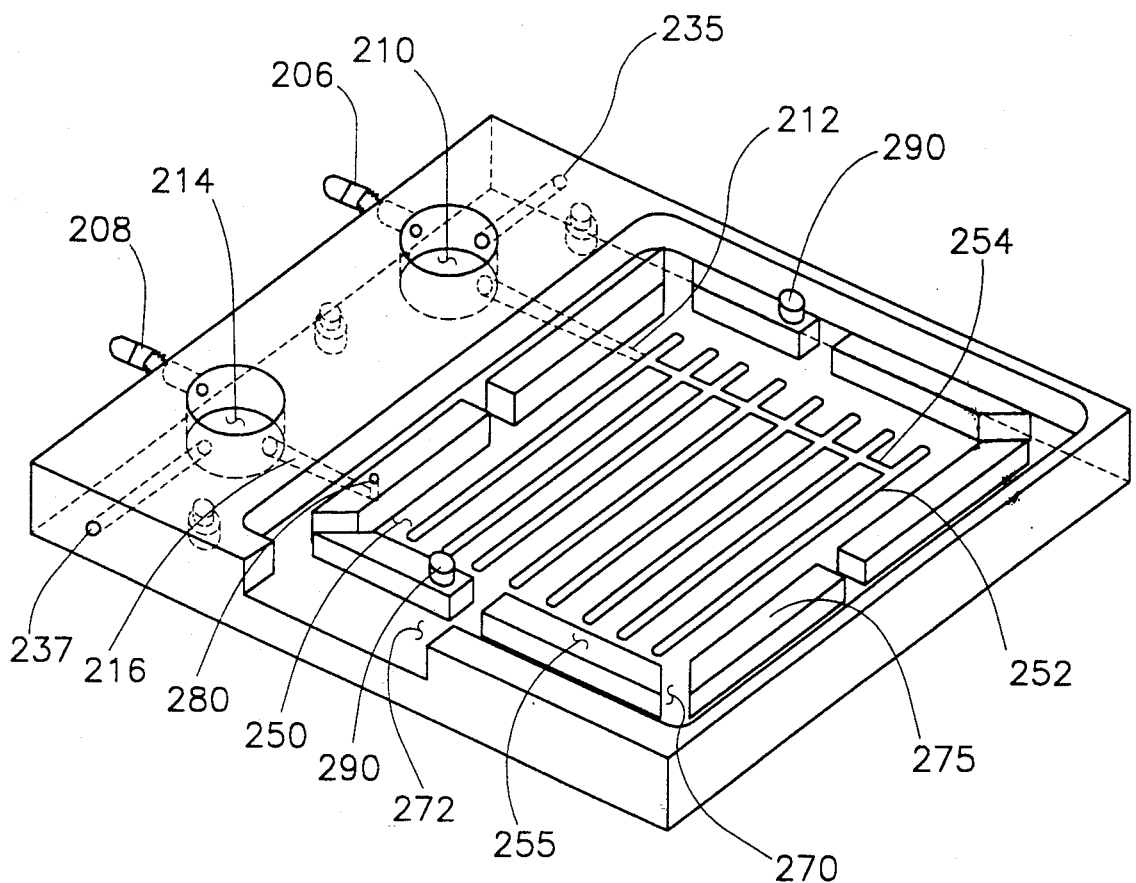
FIG. 2A is a perspective view of the base plate.
Figure 2B:
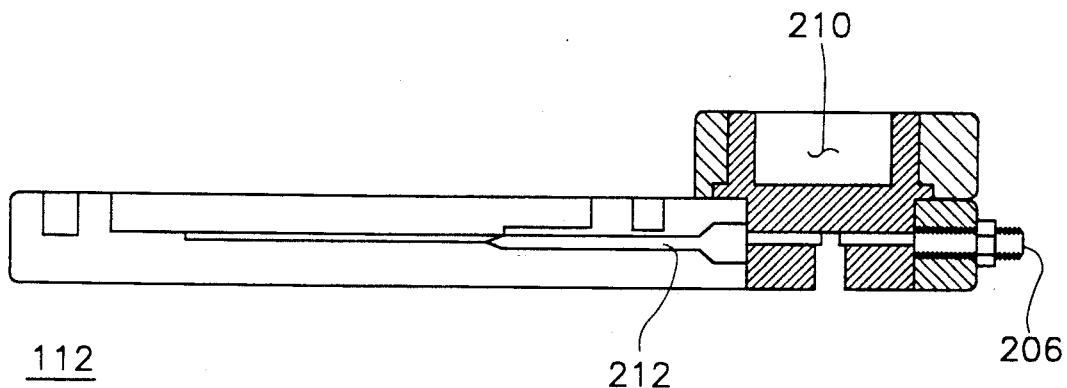
FIG. 2B is a sectional view of the base plate.

Referring now to FIGS. 2A and 2B, wherein the base plate 112 is shown in more detail. Base plate 112 comprises a first Vacuum inlet 206 and a second vacuum inlet 208. First vacuum inlet 206 and second vacuum inlet 208 enable an external vacuum source (not shown) to be connected to the apparatus 100. First vacuum inlet 206 corresponds to first vacuum feature. Second vacuum inlet 208 corresponds to the second vacuum feature. First vacuum inlet 206 and second vacuum inlet 208 are mounted via holes (not shown) in the base plate 112 by conventional mounting means.

In the preferred embodiment, first vacuum inlet 206 and second vacuum inlet 208 are quick disconnect hose barb fittings. The only important criteria is that each of vacuum inlets 206, 208 be capable of mating; and with the conventional tubing which is typically connected to the external vacuum source.

Although there are two independent vacuum features embodied in the invention, only one external vacuum source is necessary. Both first vacuum inlet 206 and second vacuum inlet 208 could be connected to the same vacuum source. A wide variety of vacuum sources may be used with the apparatus 100.

Base plate 112 further comprises a first opening 210 and a first channel 212. First opening 210 provides communication between the first vacuum inlet 206 and the first channel 212. First opening 210 is configured to accept the first vacuum valve 114. As will be shown more fully herein, rotation of the first vacuum valve 114 causes the first vacuum inlet 206 to be in and/or out of registration with the first channel 212. As will also be shown more fully herein, the first channel 212 extends into a reservoir area 250 (to be described).

Base plate 112 further comprises a second opening 214 and second channel 216. Second opening 214 is in communication with the second vacuum inlet 208 and the second channel 216. Second opening 214 is configured to accept the second vacuum valve 116. As will be shown more fully herein, rotation of the second vacuum valve 116 causes the second vacuum inlet 208 to be in and/or out of registration with the second channel 216. As will be shown more fully herein, the second channel 216 extends into a vacuum clamping area 255 (shown in FIG. 4A and to be described in conjunction therewith).

The vacuum reservoir area 250 is a recessed region within the base plate 112. The vacuum reservoir area 250 acts as a receptacle wherein a vacuum is generated to draw the sample media from the well plate 120 in contact with the filter membrane 110. The reservoir area 250 is sized so as to provide a proper vacuum area and to drain the sample media which passes through the filter membrane 110. The vacuum reservoir area 250, however, may take a variety of configurations.

The vacuum reservoir area 250 has formed therein a plurality of channels 252 equidistantly arranged. A single channel 254 connects the plurality of channels 252 to each other. Single channel 254 is provided so as to connect the channels 252 together. As will be shown more fully herein, the plurality of channels 252 that are formed in the reservoir area 250 are in registration with the openings (to be described) in the gasket 118 and the wells (to be described) of the well plate 120.

The base plate 112 has further formed therein a plurality of islands 275. As will be discussed below, the islands 275 in combination with the gasket 118 form the vacuum clamping area 255. The vacuum clamping area 255 is hereby defined as the area where the vacuum clamping means operates on the well plate 120.

The islands 275 are sized to closely receive the gasket 118. A gasket recess 270 is formed within the base plate 112, such that the top portion of gasket 118 (to be described) is at substantially the same height with the islands 275 of the base plate 112.

The base plate 112 further comprises an opening 280 positioned at the top of one island 275. Opening 280 is in communication with the second channel 216. Opening 280 introduces the clamping vacuum to the top of the island 275. As will be shown more fully herein, the well plate 120 has formed a vacuum transfer channel (to be described) which allows the vacuum present at the opening 280 to uniformly disperse throughout the top of the remaining islands 275 and those portions of the gasket 118 that lie between the islands 275.

The base plate 112 may further comprise a pair of positioning pins 290. The positioning pins 290 enable the well plate 120 to be accurately placed on top of the base plate 112, and gasket 118 when the apparatus 100 is assembled.

Figure 3:
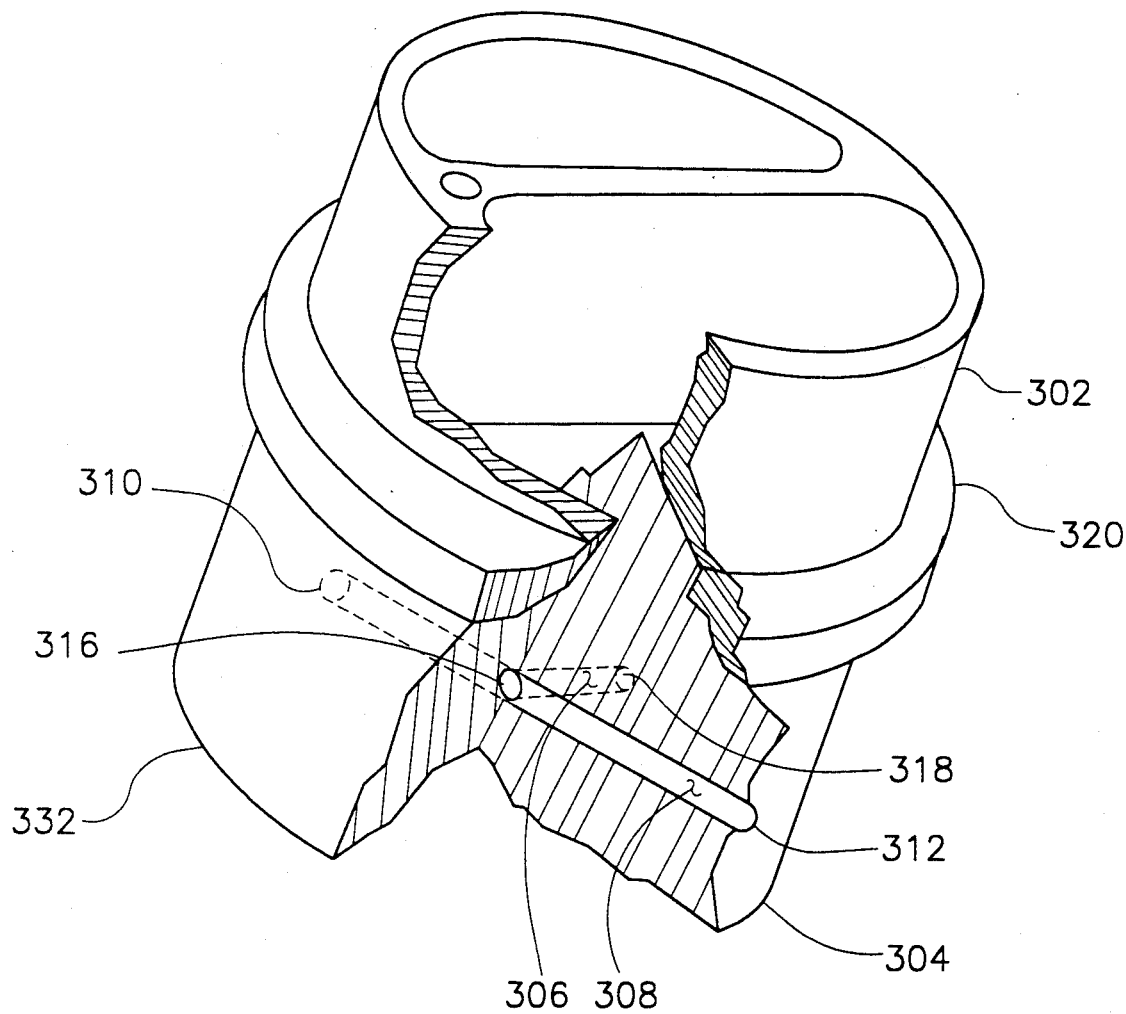
FIG. 3 is a cut-away view of the valve.

Referring now to FIG. 3, wherein the first vacuum valve 114 is shown in more detail. Generally, first vacuum valve 114 operates as a switch to turn on and off the sampling vacuum. In particularly, rotation of the first vacuum valve 114 causes the first vacuum inlet 206 to be in and out of registration with the first channel 212.

First vacuum valve 114 has an upper portion 302 and a lower portion 304. The lower portion 304 fits closely into the opening 210 of the base plate 112. A close fit is required to minimize leakage of vacuum. However, the lower portion 304 should be allowed to rotate within the opening 210.

Formed in the lower portion 304 is a first channel 306 and a second channel 308. Channel 306 has at one end a first opening 318 and at the second end a second opening 316. Channel 308 extends completely through the center of the lower portion 304. Channel 308 has at one end a first opening 310 and at the second end a second opening 312. The second opening 316 of first channel 306 intersects with the second channel 308 thus allowing communication between the first channel 306 and the second channel 308.

The lower portion is further designed such that when the openings 310 and 312 are in registration with the first vacuum inlet 206 and first channel 212 of the base plate 112, respectively, the external vacuum source (not shown) is in communication with the vacuum reservoir area 250, and thus is turned "on." When the openings 310 and 312 are not in registration with the first vacuum inlet 206 and first channel 212 of the base plate 112, the sampling vacuum is turned "off."

The lower portion is further designed such that when the opening 318 is in registration with a third channel 235 of the base plate 112, the opening 310 is in registration with the first channel 212, thus providing communication between the ambient atmosphere and the vacuum reservoir area 250. This communication allows the user to pressurize the vacuum reservoir area 250.

The first vacuum valve 114 further has formed ridge 320. Ridge 320 is configured such that it will rest on the surface of the cover plate 122. Ridge 320 ensures that the openings 310 and 312 will register with the vacuum inlet 206 and first channel 212 and that openings 316 and 318 will register with third channel 235 and first channel 212.

The second vacuum valve 116 is designed in a manner similar to that of first vacuum valve 114 described above. The second vacuum valve 116 is designed such that rotation of the second vacuum valve 116 to a first (i.e., "on") position results in communication between second vacuum inlet 208 and second channel 216 of base plate 112, thereby providing a vacuum to the vacuum clamping area 255. Rotation of the second vacuum valve 116 to a second position results in communication between a fourth channel 237 and the second channel 216 of the base plate 112, thus allowing for pressurization of the vacuum clamping area 255.

Figure 4A:
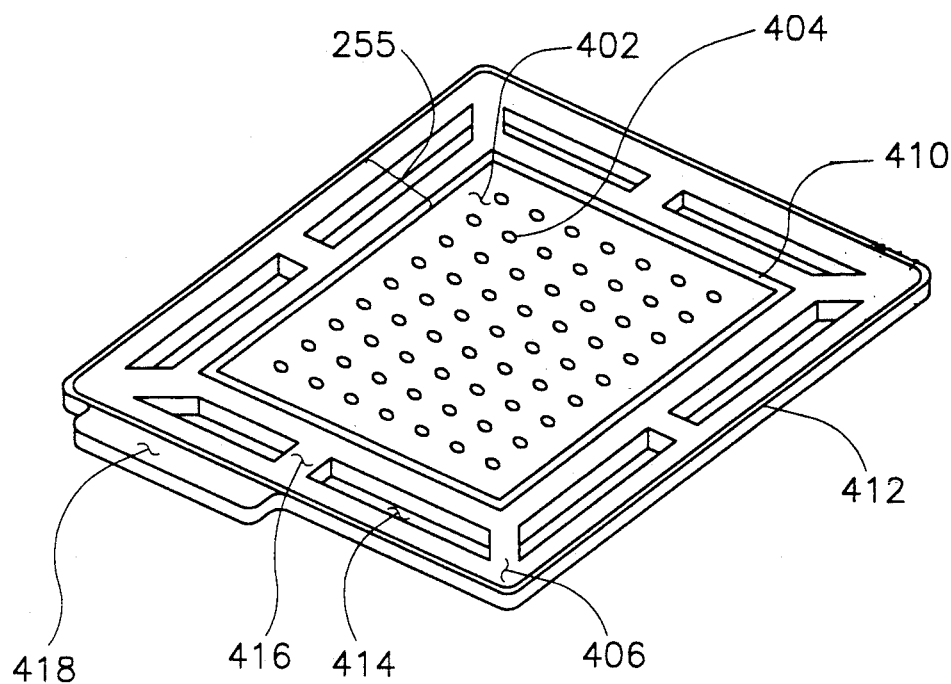
FIG. 4A is a perspective view of the gasket.
Figure 4B:
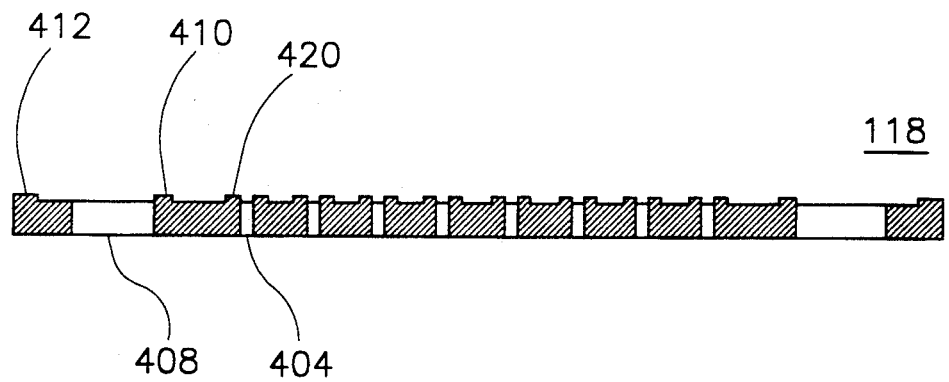
FIG. 4B is a sectional view of the gasket.

Referring now to FIGS. 4A and 4B, wherein the gasket 118 is shown in more detail. In the preferred embodiment, gasket 118 is made out of a flexible material, such as silicon or the like. In order to perform repeated filtrations with the same gasket, its material composition must be resilient. However, gasket 118 can be made out of a variety of flexible and/or resilient materials.

The gasket 118 first comprises an inner section 402. Inner section 402 has formed therein a plurality of wells 404. In the embodiment shown by FIG. 4, a standard 96 microtiter well configuration is depicted. However, the claimed invention anticipates the use of any number of wells taking a variety of shapes and sizes.

The gasket 118 further comprises a circular ridge 420 (not shown in FIG. 4A) surrounding each well 404. Each circular ridge 420 rises approximately 0.002 inches above the surface of each well 404. Each circular ridge 420 ensures, upon assembly of apparatus 100, that an airtight seal is made with a corresponding well (to be described) of the well plate 120.

The gasket 118 further comprises a webbed section 406. Webbed section 406 comprises a plurality of webs 414 and bridges 416. The webs 414 and bridges 416 are configured to mate with the islands 275 formed in the base plate 112 to thereby firmly secure the gasket 118 therein.

The gasket 118 further comprises a first border ridge 410 and a second border ridge 412. First border ridge 410 surrounds the perimeter of the inner area 402. Second border ridge 412 surrounds the perimeter of the webbed section 406. The first and second border ridges 410 and 412 are about 0.002 inch in height and upon assembly, function to define a closed vacuum clamping area 255 that will not leak vacuum.

The gasket 118 further comprises a tab portion 418. Tab portion 418 is provided to allow easy removal of the gasket 118 from the base plate 112. Tab portion 418 is configured to mate with recess 272 of the base plate 112.

Figure 5A:
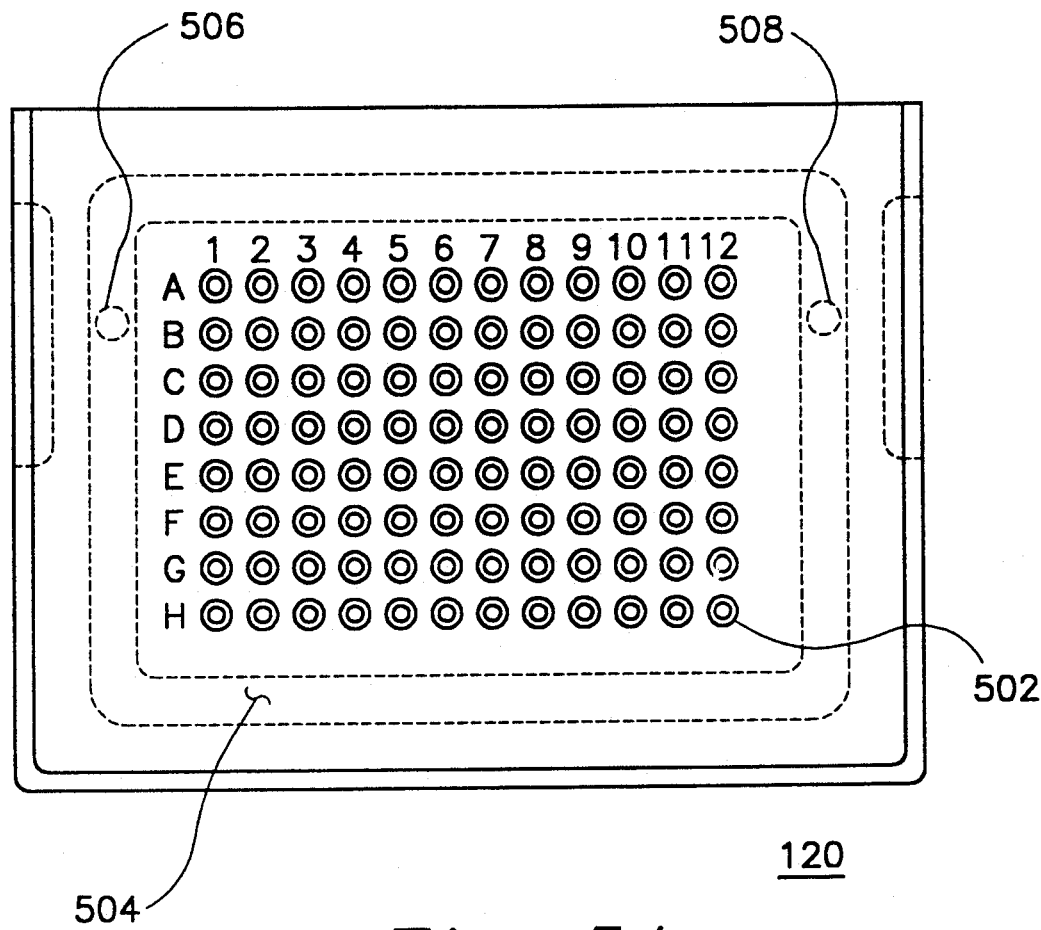
FIG. 5A is a plan view of the well plate.
Figure 5B:
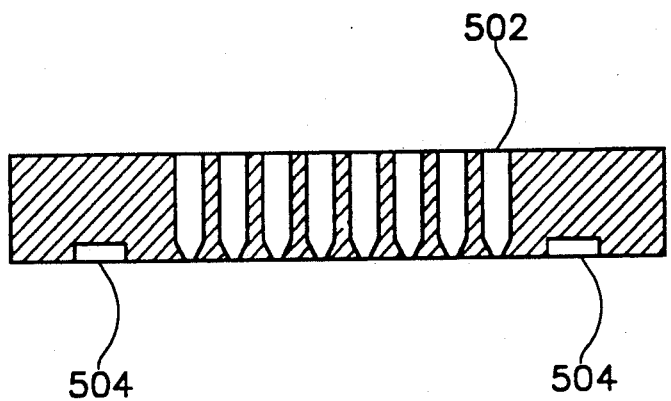
FIG. 5B is a sectional view of the well plate.

Referring now to FIGS. 5A and 5B, wherein the well plate 120 is shown in more detail. Well plate 120 first comprises a plurality of wells 502. In the embodiment shown in FIG. 5A, the wells 502 are configured in a standard 96 well microtiter configuration. However, well plate 120 could have wells of a variety of configuration depending on the type of test to be run in the apparatus 100.

The well plate 120 further comprises a recessed vacuum channel 504 extending around the perimeter of the well 502 pattern. Upon assembly, the area at the periphery of the vacuum channel 504 would be in sealable contact with the ridges 410 and 412 of the gasket 118. As such, the vacuum channel 504 becomes the ceiling for the vacuum clamping area 255 and closes it.

The well plate 120 further comprises a pair of pin insets 506, 508 to facilitate the placement of the well plate 120 with the base plate 112. Upon assembly, the positioning pins 290 of the base plate 112 mate with the pin insets 506 and 508, respectively.

The operation of the present invention will now be described.

Initially, the first vacuum valve 114 is set to the "release" position and the second vacuum valve 116 is set to the "off" position. As such, operation of the apparatus 100 can now begin. The external vacuum source is assumed to be on.

The gasket 118 is first placed onto the base plate 112. The plurality of webs 414 and bridges 416 mate with the corresponding islands 275 on the base plate.

Thereafter, the filter membrane 110 is placed on the inner section 402 of the gasket 118.

Thereafter, the well plate 120 is placed on the base plate 112 via mating pins 290 and insets 506 and 508. Upon placement of the well plate 120 on the base plate 112, the wells 502 of the well plate 120 are in substantial registration with the wells 404 of the gasket 118. Furthermore, the channels 252 of base plate 112 are positioned directly under the wells 404 of the gasket 118.

At this point, the apparatus 100 is ready to be clamped into position. The second vacuum valve 116 is rotated to the "on" position. As a result, the well plate 120 is forced into contact with the upper surface of the islands 275 and the ridges 410 and 412 of the gasket 118. The gasket 118 conforms with any irregularities found on the surface of well plate 120. The circular ridges surrounding the wells 502 of the gasket 118 are also compressed, thereby providing complete separation between the individual wells 502 of the well plate 120 on the filter membrane 110. Complete isolation of the wells 502 on the membrane 110 eliminates bleeding or migration of sample media across the filter membrane 110.

After a short period of time, the vacuum clamping force reaches maximum and the apparatus 100 is fully clamped. In this position, the ridges 410 and 412 of the gasket 118 are in sealable contact with the well plate 120 and the vacuum clamping area 255 is fully enclosed by the islands 275, the ridges 410 and 412, and the vacuum channel 504 of the well plate 120.

Thereafter, the filtration process can begin. Sample media may be loaded into the wells 502 of the well plate 120. Thereafter, the filtration process is initiated by rotating the first vacuum valve 114 to the "on" position. Rotation of the first vacuum valve 114 to the "on" position causes a vacuum to come about in the vacuum reservoir area 250. As such, the sample media contained in the wells 502 of the well plate 120 are brought into contact with the filter membrane 110. Sample media that passes through the filter membrane 110 is discharged through the vacuum reservoir area 250 and out the channel 212 and first vacuum inlet 206.

Upon completion of the filtration process, the user rotates the first vacuum valve 114 to the "off" position. In the "off" position, external vacuum source is disengaged from the vacuum reservoir area 250 and moreover, the vacuum reservoir area 250 is in communication with the surrounding ambient environment. This pressurizes the vacuum reservoir area 250 thereby stopping the drainage of sample media from the wells 502 of the well plate 120.

Thereafter, the user has two options. First, the user can re-load the well plate 120 with additional and/or different sample media. Because the second vacuum valve 116 is still in the "on" position, the user can not remove the well plate 120 and as such any re-loading of sample media would have to be done with the well plate 120 still in place.

Alternatively, and possibly more likely, the user may want to remove the filter membrane 110 for further testing or the user may want to remove only the well plate 120 and replace it with an additional well plate 120 containing additional and/or different sample media to be tested with the existing sample media filtrate which is already present on the filter membrane 110. In either case, the user has to rotate the second vacuum valve 116 to the "release" position. Rotation of the second vacuum valve 116 to the "release" position causes the external vacuum source to be disengaged from the vacuum clamping area 255 and the vacuum clamping area 255 to be in communication with the surrounding ambient environment. As such, this pressurizes the vacuum clamping area 255 thereby releasing the clamping force holding the apparatus 100 together.

At this point, the well plate 120 can be removed and replaced with another well plate 120 without removing the filter membrane 110. Alternatively, the user can remove the well plate 120 and the filter membrane 110. The filter membrane 110 can then be further tested as desired. Additionally, the gasket 118 can be removed by lifting up the tab 418 on gasket 118. The gasket 118 can then be cleaned and replaced on the base plate 112 for use in the next test. Alternatively, a different gasket 118 can be placed thereon.

In contrast to conventional devices, the present invention can draw the sample media into contact with the filter membrane in an uncontaminated manner. The vacuum clamping feature of the present invention acts to isolate each well pattern on the filter membrane thereby eliminating sample media migration or so called bleeding that occurs in conventional apparatus. Furthermore, the apparatus of the present invention can be quickly assembled and disassembled thus increasing test production output and efficiency.

It will be apparent to one of skill in that art, that numerous modifications and/or alternative embodiments of the present invention heretofore described are possible. Such modifications and/or alternative embodiments may include, but are not limited to, an additional channel formed in the well plate 120 so as to allow the space surrounding the annular ridge 420 of each well 404 in gasket 118 to be in communication with the ambient environment. This would guard against evacuation of this area in the event of an imperfect performance of the first border ridge 410 once the vacuum clamp is applied and in effect. Vacuum in this area would increase the likelihood of cross-well migration of samples.

The foregoing description is intended primarily for purposes of illustration. The present invention may be embodied in other forms or carried out in other ways without departing from the spirit or scope of the invention. Modifications and variations still falling within the spirit or the scope of the invention will be readily apparent to those of ordinary skill in the art.

What is claimed is:

1. An apparatus for filtering a plurality of liquid samples using a filter membrane and for preventing cross-contamination by migration of the liquid samples along the filter membrane, the apparatus comprising:
   (a) a well plate having a plurality of wells for receiving the liquid samples, said well plate having a substantially flat upper surface and a substantially flat lower surface, wherein each of said plurality of wells has a top opening in said upper surface and a bottom opening in said lower surface;
   (b) a base plate having a substantially flat upper surface constructed and arranged to mate with said lower surface of said well plate;
   (c) first vacuum means for vacuum-clamping said well plate to said base plate with the filter membrane disposed therebetween such that the filter membrane is held in sealable contact with said bottom openings of said plurality of wells of said well plate to preclude leakage of the liquid samples from said plurality of wells except through the filter membrane and to substantially preclude migration of the liquid samples between said wells along the filter membrane; and
   (d) second vacuum means for drawing the liquid samples contained in said plurality of wells through the filter membrane, said second vacuum means being coupled to said bottom openings of said plurality of wells, through the filter membrane, when said first vacuum means clamps said base plate to said well plate.

2. The apparatus of claim 1, further comprising a flexible, resilient gasket disposed between said well plate and said base plate, said gasket isolating action of said first vacuum means from action of said second vacuum means.

3. The apparatus of claim 1, wherein said first vacuum means comprises a vacuum clamping area formed at a peripheral edge of said upper surface of said base plate and a peripheral edge of said lower surface of said well plate, said vacuum clamping area constructed and arranged to vacuum-clamp said well plate to said base plate when a vacuum is created in said vacuum clamping area.

4. The apparatus of claim 3, wherein said second vacuum means comprises a vacuum reservoir area formed at a central portion of said upper surface of said base plate, said vacuum reservoir area constructed and arranged to create a vacuum at said bottom openings of said plurality of wells of said well plate when said well plate is vacuum clamped to said base plate by said first vacuum means.

5. The apparatus of claim 4, further comprising:
   election means for operating said second vacuum means independently of said first vacuum means.

6. The apparatus of claim 5, wherein said election means comprises a vacuum clamping valve disposed on said base plate and connectable to an external vacuum source to selectively create a vacuum in said vacuum clamping area and a vacuum sampling valve disposed on said base plate and connectable to an external vacuum source to selectively create a vacuum in said vacuum reservoir area.

7. The apparatus of claim 6, wherein said first vacuum means and said second vacuum means further comprise a flexible, resilient gasket disposed between said filter membrane and said base plate, said gasket isolating said vacuum clamping area, isolating said vacuum sampling area, and maintaining the filter membrane in sealable contact with each of said plurality of wells of said well plate.

8. An apparatus for filtering a plurality of liquid samples, the apparatus comprising:
   (a) a well plate having a plurality of wells for receiving the liquid samples, said well plate having a substantially flat upper surface and a substantially flat lower surface, wherein each of said plurality of wells has a top opening in said upper surface and a bottom opening in said lower surface;
   (b) a base plate having a substantially flat upper surface constructed and arranged to mate with said lower surface of said well plate;
   (c) a filter membrane disposed between said lower surface of said well plate and said upper surface of said base plate;
   (d) first vacuum means for vacuum-clamping said well plate to said base plate and for holding said filter membrane in sealable contact with said bottom openings of said plurality of wells of said well plate to substantially preclude leakage of the liquid samples from said plurality of wells except through said filter membrane and to substantially preclude migration of the liquid samples between said plurality of wells along said filter membrane; and
   (e) second vacuum means for drawing the liquid samples contained in said plurality of wells through said filter membrane, said second vacuum means being coupled to said bottom openings of said plurality of wells, through said filter membrane, when said first vacuum means clamps said base plate to said well plate.

9. The apparatus of claim 8, further comprising a flexible, resilient gasket disposed between said filter membrane and said base plate, said gasket isolating action of said first vacuum means from action of said second vacuum means.

10. The apparatus of claim 8, wherein said first vacuum means comprises a vacuum clamping area formed at a peripheral edge of said upper surface of said base plate and a peripheral edge of said lower surface of said well plate, said vacuum clamping area constructed and arranged to vacuum-clamp said well plate to said base plate when a vacuum is created therein.

11. The apparatus of claim 10, wherein said second vacuum means comprises a vacuum reservoir area formed at a central portion of said upper surface of said base plate, said vacuum reservoir area constructed and arranged to create a vacuum at said bottom openings of said plurality of wells of said well plate when said well plate is vacuum clamped to said base plate by action of said first vacuum means.

12. The apparatus of claim 11, further comprising:
   election means for operating said second vacuum means independently of said first vacuum means.

13. The apparatus of claim 12, wherein said election means comprises a vacuum clamping valve disposed on said base plate and connectable to an external vacuum source to selectively create a vacuum in said vacuum clamping area and a vacuum sampling valve disposed on said base plate and connectable to an external vacuum source to selectively create a vacuum in said vacuum reservoir area.

14. The apparatus of claim 13, wherein said first vacuum means and said second vacuum means further comprise a flexible, resilient gasket disposed between said filter membrane and said base plate, said gasket isolating said vacuum clamping area, isolating said vacuum sampling area, and maintaining said filter membrane in sealable contact with each of said plurality of wells of said well plate.

15. An apparatus for filtering a plurality of liquid samples, the apparatus comprising:
(a) a base plate having a substantially flat upper surface, said base plate including a first vacuum inlet, a second vacuum inlet, a vacuum clamping valve, and a vacuum sampling valve, said base plate partially defining a vacuum clamping area and a vacuum reservoir area, said first vacuum inlet being coupled to said vacuum clamping area through said vacuum clamping valve to selectively create a vacuum in said vacuum clamping area, said second vacuum inlet being coupled to said vacuum reservoir area through said vacuum sampling valve to selectively create a vacuum in said vacuum reservoir area;
(b) a well plate removably mounted on said base plate and having a substantially flat lower surface constructed and arranged to mate with said upper surface of said base plate when said well plate is mounted on said base late, said well plate having a plurality of sample wells, each of said plurality of sample wells including a top opening for receiving the liquid samples and a bottom opening in said lower surface in communication with said vacuum reservoir area of said base plate;
(c) a filter membrane, through which the liquid samples are to be filtered, disposed between said upper surface of said base plate and said lower surface of said well plate, said filter membrane being positioned between said bottom openings of said sample wells and said vacuum reservoir area of said base plate; and
(d) a flexible, resilient gasket disposed between said filter membrane and said upper surface of said base plate, said gasket isolating said vacuum clamping area from communication with said vacuum reservoir area and maintaining a seal between said lower surface of said well plate and said vacuum clamping area of said base plate so that said base plate is vacuum clamped to said well plate when a vacuum is created in said vacuum clamping area via said first vacuum inlet and said vacuum clamping valve, said gasket further maintaining said filter membrane in sealable contact with said bottom openings of said plurality of sample wells of said well plate to substantially preclude migration of the liquid samples between said wells along said filter membrane when the liquid samples are drawn through said filter membrane by action of a vacuum created in said vacuum reservoir area via said second vacuum inlet and said vacuum sampling valve.

16. The apparatus of claim 15, wherein said gasket includes first and second substantially parallel elastomeric surfaces and a plurality of well openings corresponding to respective ones of said bottom openings of said plurality of sample wells of said well plate.

17. The apparatus of claim 16, wherein said vacuum clamping area of said base plate includes a plurality of raised islands which extend upward from said upper surface of said base plate, and wherein said gasket includes a plurality of webs and bridges constructed and arranged to mate with respective ones of said islands.

* * * * *